United States Patent [19]
Bell

[11] 3,966,925
[45] June 29, 1976

[54] LUBRICANT FOR FITTING AND TRIAL MOUNTING OF PROSTHODONTIC APPLIANCES

[76] Inventor: Arthur Milton Bell, 211 Chadwick Road, Teaneck, N.J. 07666

[22] Filed: Dec. 24, 1974

[21] Appl. No.: 536,270

Related U.S. Application Data

[60] Division of Ser. No. 326,575, Jan. 26, 1973, Pat. No. 3,861,041, which is a continuation-in-part of Ser. No. 184,949, Sept. 29, 1971, abandoned.

[52] U.S. Cl. .............................. 424/240; 424/181; 424/114
[51] Int. Cl.² ...................................... A61K 31/56
[58] Field of Search ..................... 424/181, 114, 240

[56] References Cited
UNITED STATES PATENTS 3,177,230  4/1965  Hogg et al. ................... 260/397.45
3,255,079  6/1966  Schroeder et al. ................... 424/240

*Primary Examiner*—Elbert L. Roberts
*Attorney, Agent, or Firm*—Ralph R. Roberts

[57] ABSTRACT

This invention provides a lubricating compound for the fitting of crowns, bridges and other prosthodontic restorations as used in prosthodontic dentistry. This compound in a preferred embodiment has a base which comprises 90 or more percent of the compound. A coloring agent which may be zinc oxide is five percent or less of the compound while small percentages of a bacteriostatic agent and an anti-inflammatory agent make up the rest of the compound. The compound is preferably readily washed from the prepared teeth and restoration after a try-in of the unfinished crown, bridge or other prosthodontic restoration has been done. This lubricant provides a new testing technique to be employed for the duration of the trial period of the restoration.

10 Claims, No Drawings

LUBRICANT FOR FITTING AND TRIAL MOUNTING OF PROSTHODONTIC APPLIANCES

CROSS-REFERENCE TO RELATED APPLICATION

This application is a Divisional Application of my parent application, Ser. No. 326,575, filed Jan. 26, 1973 and entitled, "Lubricant and Method of Fitting and Trial Mounting of Prosthodontic Appliances", now U.S. Pat. No. 3,861,041 which application was a Continuation-in-Part of U.S. patent application Ser. No. 184,949, filed Sept. 29, 1971 now abandoned in the name of A. Milton Bell and entitled, "Lubricant for the Fitting and Trial Mounting of Prosthodontic Appliances".

Restriction was required in the Patent Office Action mailed Jan. 22, 1974.

BACKGROUND OF THE INVENTION

Classification of the Art

In accordance with the classification of art as established in the U.S. Patent Office the present invention pertains to the general Class of "Drugs, Bio-Affecting and Body Treating Compounds" (Class 424) and more particularly to the subclass of "plural fermentates of different origin" (subclass 114).

Still in this same drug class may be classed the added anti-inflammatory agent which is preferably included in the lubricant compound. This agent is preferably a steroid organic compound. As other anti-inflammatory agents may be used as well as synthetic anti-inflammatory agents a portion of the prior art should be found in the subclass generally identified as "organic active ingredient" (subclass 167).

DESCRIPTION OF THE PRIOR ART

In the fitting of copings, full crowns, inlays, permanent bridges and the like, the dentist has customarily fitted or tried-in the unfinished prosthodontic restoration on the tooth preparation without the benefit of any lubricating material.

The dentist, in so doing, is oftentimes handicapped in this procedure by tenso-frictional or other interferences such as is known in the dental profession as contact points with adjacent teeth, parallelism of abutments, path of insertion, etc. These interferences act to prevent the proper seating of the dental restoration upon or within the tooth preparation as the case may be.

After the initial fittings and try-in of the restoration or restorations, the restorative appliance is finished and readied for the final insertion. Some dental practitioners may employ so called temporary cements for insertion of the appliance during a trial or test period. These temporary cements set to various degrees of hardness thereby acting as further interferences to the complete seating of the finished restoration. Thus, the incompletely seated restoration is often overadjusted, especially on the biting surfaces, in order to achieve a comfortable biting pattern for the patient (relief of interocclusal interferences) and/or improper contact points and marginal discrepancies. These marginal discrepancies can lead to washing out of the final cement media, periodontal inflammatory processes and possible recurrent decay at the margins of the restoration.

It is an accepted fact that dental procedures which require the cutting of the tooth surface into the dentinal area for the placement of fillings, inlays, crowns, etc., utilizing the best accepted techniques and instrumentation, results in an increase in sensitivity of the prepared tooth to thermal changes, chemical agents and mechanical stimuli. This is due to the insult of the pulpal tissues of the tooth in response to the operative procedure. This response is generally due to a hyperemia resulting in an increase in pressure within the confines of the hard structures which comprise the pulpal chamber and canal of the tooth.

In order to control this inflammatory response and facilitate the treatment program and render the patient more comfortable, the inventor has incorporated an anti-inflammatory agent into a lubricating compound which in turn acts as a desensitizing agent upon the tooth by reduction of the hyperemic response of the pulpal tissues.

The inventor, in order to better fit the restorations used in crown and bridge dentistry has, instead of the difficult to remove temporary cement, provided in this invention a lubricating compound which is easily dispensed and which provides additional desirable side effects which enhance and facilitate the practice of crown and bridge dentistry. This lubricating compound does not "set" during its use, hence a more accurate initial fit as well as a final better dental restoration is provided. This lubricating compound permits the placement and resting of the final restoration on its support. This placed final restoration may then be observed in function so that the restoration has a period of settling permitting the restoration and its environs to come to equilibrium prior to the final cementation of the appliance.

This lubricant provides a new technique in the mounting of prosthodontic appliances for permitting the final dental restoration to be temporarily mounted on the prepared tooth or teeth during a trial period; the lubricant having substantially no change in physical characteristics during the trial period and at the end of this period the lubricant is readily flushed from the restoration and tooth or teeth prior to the final cementation.

SUMMARY OF THE INVENTION

This invention may be summarized at least in part with reference to its objects.

It is an object of this invention to provide, and it does provide, a lubricating compound of active and inert substances which permit the fitting of crowns and bridges to a prepared tooth or teeth while preventing noxious odor forming bacteria from infiltrating the crown or bridge retainers while they are in the mouth and during this period of provisional function the dentist is able to observe the restoration during this trial period.

It is a further object of this invention to provide, and it does provide, a lubricating compound which is useful in fitting crowns and other prosthodontic restorations to the prepared tooth or teeth, said compound in addition to the base lubricant material providing also a desensitizing agent as well as an anti-inflammatory agent.

It is a still further object of this invention to provide, and it does provide, a lubricating compound for the improved fitting of crowns, bridges and other restorations in the practice of dentistry, said compound having a base which is a natural or synthetic type lubricant which is sufficiently stiff to be resistant to flow. This base is water soluble and to insure sufficient coloration, a coloring material such as zinc oxide may be added if necessary. A small amount of a bacteriostatic agent and an anti-inflammatory agent is also provided in the compound.

The compound of this invention is preferably readily and easily cleansed from the retainers and prepared teeth by lavaging with warm water, as by rinsing and/or with a warm water syringe. This lubricant permits a new and improved method of a try-in and trial period to be useful in prosthodontic dentistry.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen specific embodiments of the lubricant for fitting crowns and bridges as adopted for use in prosthodontic dentistry. These specific embodiments have been chosen for the purpose of illustration and description in the following detailed description.

DESCRIPTION OF THE PREFERRED EMBODIMENTS

The lubricant of this invention is a new compound particularly for use in dentistry and as such must use ingredients which are non-toxic and acceptable to the Federal Drug Administration for use in the mouth of a patient. As the compound may be infrequently used and then in only small amounts it is desirable that the compound have a safe shelf life of at least a year and preferably for a much greater length of time such as 5 years.

Compounds having such properties include:

I.
| | | |
|---|---|---|
| Base Material | Aqualose | 95%+ |
| Added Color | Zinc Oxide | 2%+ |
| Bacteriostatic Agent | Neomycin | 1%+ |
| Anti-inflammatory Agent | Fluocinolone Acetonide | 1/4 – 1/20% |

Note: Aqualose is a tradename for Ethoxylated Cholesterol made by Stephen Chemical Company of Maywood, New Jersey. Fluocinolone Acetonide is a fluoride compound made by Syntex Laboratories of Palo Alto, California.

II.
| | | |
|---|---|---|
| Base Material | Solulan 24 | 88%+ |
| | Amerchol-L101 | 10%+ |
| Bacteriostatic Agent | Neomycin | 1%+ |
| Anti-inflammatory Agent | Fluocinolone Acetonide | 1/4 – 1/20% |

The base materials are manufactured by American Cholesterol Company of Edison, New Jersey.

III.
| | | |
|---|---|---|
| Base Material | Lipolan | 98%+ |
| Bacteriostatic Agent | Neomycin | 1%+ |
| Anti-inflammatory Agent | Fluocinolone Acetonide | 1/4 – 1/20% |

The base material Lipolan is a hydrogenated lanolin made by Lipo Chemical, Inc., 114 East 32nd Street, New York, New York 10016.

IV.
| | | |
|---|---|---|
| Base Material | Plastibase | 97%+ |
| Color | Zinc Oxide | 1%+ |
| Bacteriostatic Agent | Neomycin | 1%+ |
| Anti-inflammatory Agent | Fluocinolone Acetonide | 1/4 – 1/20% |

The base compound I (Aqualose) has the desirable properties of having a detergent action and is both water and alcohol soluble.

In the above compounds instead of neomycin the bacteriostatic agent may be hexochlorophene but the base material must be reduced slightly to permit the hexochlorophene to be about 2½%. It is also to be noted that "Bacitracin" as manufactured by Upjohn of Kalamazoo, Michigan may be used in place of neomycin.

In the above, instead of Fluocinolone Acetonide as the anti-inflammatory agent, hydrocortisone about 1½% may be used.

In all compounds the consistency must be such as to be a non-flowing grease which will remain where placed until displaced or removed by lavaging with warm water.

ALTERNATE COMPOUNDS

As an alternate material for the base materials above the following materials have been tried:

1. Petrolatum jelly (for example, "Vaseline", TM of Chesebrough-Ponds, Inc., 485 Lexington Avenue, New York, N.Y. 10017). Although a good lubricant it is not as desirable as the base materials above listed. Petrolatum is difficult to clean from both the restoration and the prepared teeth and any residue of the lubricant interferes with the final permanent cementation of the prosthodontic restoration, which is a critical step of this method of treatment. The petrolatum also is a media for bacterial growth which is a cause for noxious odors and putrefaction and bad tastes in the oral environs.

2. Aquaphor; a basic anhydrous vehicle used in pharmaceutical preparations and a trademarked product manufactured and sold by Duke Laboratories, Inc., P.O. Box 529, South Norwalk, Connecticut 06856. This substance is similar to and appears to have the characteristics of anhydrous lanolin.

3. Neobase (TM of Burroughs Wellcome & Company, 1 Scarsdale Road, Tuckahoe, New York 10707). This greaseless ointment is a manufactured material which is white in color making it easily visible for cleaning purposes and eliminates the need of the zinc oxide in example I. The petrolatum, aquaphor and anhydrous lanolin are clear and relatively colorless thereby making it very desirable to add a coloring agent such as zinc oxide to the compound so that the dentist can view both the application and removal of the compound from the restoration and the prepared teeth. "Neobase" is a carboxy methyl cellulose material in a plasticized hydrocarbon jell and is easily removed from the restoration and prepared teeth. This material appears to be a superior base material but has been used in experimental tests for only a few months.

Other waxes, oils and greaseless compounds can undoubtedly be used instead of the above-suggested base materials; however, it is necessary that they be approved for use in a human mouth and also that they be easily and completely removed from both the restorations and prepared teeth and that said surfaces be easily conditioned for permanent cementation of the restoration.

-continued
| | | |
|---|---|---|
| Anti-inflammatory Agent | Fluocinolone Acetonide | 1/4 – 1/20% |

The bacteriostatic agent above-mentioned is Neomycin sulfate 1%. Other agents are also effective in stabilizing the compound and preventing bacterial growth leading to the production of noxious odors, etc. Perhaps the most important function of the bacteriostatic agent is to prevent the proliferation of the acid forming bacteria (acidophilus) which leads to sensitivity and possible decay, or plaque formation.

The anti-inflammatory agent described in the preferred embodiment is Fluocinolone Acetonide, a synthetic steroid which in a very small amount such as less than one-quarter of 1 percent and as little as one-twentieth of 1 percent is effective in keeping the inflammation in control. Also usable as an anti-inflammatory agent is hydrocortisone acetate which is available from Merck, Sharp and Dohme of West Point, Pennsylvania 19486. This is also available as "prednisolone" which, as a antiphlogistic drug, is available from McKesson (Division of McKesson & Robbins, Inc., Bridgeport, Connecticut 06602) and also from Rexall Drug Company, Rexall Square, Los Angeles, California 90054. There are many such antiphlogistic drugs now available and these are used in approved opthalmic and dermatological ointments in dosages similar to the lubricant compound of this invention. The small amount used in the lubricating compound is infinitesimal compared to ordinary dosages prescribed in several medical therapeutics.

USE OF THE LUBRICANT

After the teeth have been prepared in the customary manner and the restoration has been formed in the usual manner such as by casting, the dentist applies a coating of the lubricant of this invention to the mating cavity surfaces of the restoration. Said restorations are customarily tried-in (i.e., inlays and inlay-type or pin-type restorations) or fitted upon the prepared tooth (i.e., a coping or crown-type of restoration). The cast, unfinished restoration requires adjustments prior to finishing and the lubricant has the twofold purpose of helping to seat the restoration in place as well as to act as an anti-inflammatory agent thereby reducing the sensitivity of the tooth to the mechanical procedure.

The prepared tooth is carefully dried and the restoration is then coated with the lubricant and seated in position. It is known that when a dentist restores even a single jacket crown or inlay it will usually feel high to the patient. This is due to the changes in the proprioceptor impulses of the periodontium. In particular, the change from any temporary crown or restoration (generally a soft material such as acrylic plastic) to the final restoration, which is properly built to the occlusion, will feel strange and high to the patient.

After the restoration is finished and readied for insertion the lubricant of this invention permits a provisional seating of this final restoration to be made and following this test period the strange feeling experienced by the patient for the new restoration usually subsides. This strange feeling is soon accommodated as the neuro-muscular mechanism is retrained to the restored bite relationship caused by the new restoration. The patient, after a short trial period, will report that the restoration is comfortable and any minor adjustments or changes are easily made upon the restoration since it can be easily removed due to the lubricant compound. The restoration can then be refined and/or refinished prior to the final cementation or placement. This technique using one of the lubricants above-described helps obviate the necessity of grinding the occlusal anatomy of the finished restoration in order to remove interocclusal interference (high spots) which are most often caused by incomplete seating of the restoration upon final cementation. It is also noted that the test period of the final restoration provided by this lubricant enables the dentist to observe the gingival response to the new environment provided by the new restoration.

REDUCTION TO PRACTICE OBSERVATIONS

The inventor is a practicing dentist specializing in prosthodontics and oral diagnosis and has made extensive tests of this type of lubricant and has found that his patients greatly appreciate the improved results provided by the lubricant of this invention. Generally, when first seated, subgingival restorations cause a mild blanching of the marginal gingiva. Supragingival restorations do not manifest the gingival blanching but may show some minor discrepancies such as incomplete seating of one or more retainers. These discrepancies are especially noted in long span splints and bridges wherein one may find some spring or movement of the restoration and perhaps some difficulty in completely seating the fixed prosthodontic appliance.

If the final restoration fulfills all of the requirements of a satisfactory fitting and a good prosthodontic restoration, then the internal surfaces of the appliance are generously covered with one of the lubricating compound above-described. This is in lieu of any of the so-called temporary cements or hardening substances. The patient is then instructed to clench the jaws on cottom rolls intermittently for a period of approximately 2 hours and to chew on any non-sticky hard foods normally eaten. The patient is dismissed for a minimum of 24 hours but can go for much longer periods of time; for example, for a period of 72 hours which is a reasonable period for observation and evaluation of the physiological responses. On short spans and individual retainers and crowns a short time period such as 24 hours may be used to permit initial examination and minor adjustments after which longer periods can be used once it is ascertained that the patient is comfortable.

After this short test period the bite and contact points can be checked and occlusal adjustments, which are usually minimal, can be made if the original laboratory procedures and bite registrations are carefully performed.

When the restoration is removed the periodontal response can be examined. Impingement or entrapped free gingiva is an indication of a poor fitting retainer. Overextended margins leave telltale clues of inflammatory tissue as the lubricating compound will not mask any faults but will clearly show any possibilities of future inadequacies of the restoration. When the restoration is a satisfactory fit on subgingival retainers, upon removal of the appliance there is clearly outlined the gingival border of the retainer as it fits the tooth. This is manifested by a normal healthy gingival tone and color.

Supragingival retainers where the restoration has fully seated itself shows all margins properly covered and a complete lack of marginal discrepancies. Removal of the appliance is easy to accomplish and replacement poses no problems since the abutment teeth have had an opportunity to align and adjust to the final restoration. The subgingival retainers show that the healthy gingiva follows the outline of the tooth preparation and one can follow the surface epithelium of the marginal gingiva as it follows the internal surface of the gingival sulcus. The dentist can often look into the gingival sulous which was provided for in the preparation and impression steps. As above-noted the lubricating compound is easily rinsed from the restoration and prepared teeth by lavaging with warm water.

The inclusion of the anti-inflammatory agent as a part of the lubricating compound is a benefit to the patient for all steps in the restoration. The marked effect of desensitizing the prepared tooth by this anti-inflammatory agent facilitates the treatment program during the try-in period of the temporary crowns; the try-in period of the unfinished castings and copings, and finally in the provisional seating of the final finished restoration.

In addition, the active ingredients of the lubricating compound have been found to have a desirable effect upon the gingival tissue which is beneficially treated by the anti-inflammatory agent when the compound is massaged into the tissues surrounding the tooth preparation prior to lavaging with a warm water syringe or having the patient rinse the mouth.

The desensitizing effect of the anti-inflammatory agent upon the pulpal tissue of the prepared tooth facilitates the final cementation technique which customarily utilizes the present formulation of oxyphosphate powder and oxyphosphoric acid liquid. This cement is very irritating to the pulpal tissue and to relieve the pain the dentist often has to give the patient a local anesthetic. The lubricating compound above-described desensitizes the pulpal tissue sufficiently so that the final cementation may be done without undue discomfort from the cement application thus avoiding the use of an anesthetic.

It is to be further noted that lubricant compounds where the lubricant base is a glycol compound may, of itself, provide the necessary bacteriostatic effect so that the added bacteriostatic agent above-noted may be eliminated from the compound which will then have the necessary means to prevent bacterial proliferation in the environs of the mouth.

Conventional mounting of temporary crowns and unfinished restorations by means of temporary cements result in mountings which are very difficult to remove and may cause pain and/or damage. The lubricant of this invention permits the mounted appliance, whether a temporary crown, an unfinished casting or coping or the final finished restoration, to be easily removed from the prepared teeth. The lubricant prevents the seizure and adherence presently experienced in the use of temporary cements or fillers which "set" up in a period of a few minutes. As the lubricant of this invention does not take a "set" the appliance is easily removed by the dentist with no damage, pain or inconvenience. After observation of all the fitting factors the dentist removes the lubricant as by a rinse of warm water.

For the convenience of claim definition the term "restoration" includes all prosthodontic appliances such as crowns, caps, inlays and the like above-noted. These restorations, conventionally, are cast or otherwise formed and are usually preliminarily fitted to a prepared tooth prior to the step of final cementation. Where a final cementing process is to be employed after the trial fitting adjustments have been achieved, the use of the lubricant of the invention is quite helpful. This use is particularly beneficial where pain during a trial fitting is encountered.

While a particular embodiment of the lubricating compound and alternate embodiments have been described it is to be understood the invention is not limited thereto since modifications may be made within the scope of the accompanying claims and protection is sought to the broadest extent the prior art allows.

What is claimed is:

1. A lubricating compound for the fitting, trial mounting and removal of prosthodontic appliances, said compound including: (a) a stable, non-toxic, non-setting, water soluble, greaseless base material providing at least 80 percent of the compound, said base material being characterized as having a lubricating quality which quality is not materially affected by storage under reasonable conditions and also during intimate contact with the environs of the mouth, appliance and teeth preparations, said base having a consistency sufficiently stiff to prevent fluid flow by gravity; (b) an anti-inflammatory agent provided by Fluocinolone Acetonide of less than one-quarter of 1 percent of the compound and sufficient to provide a desensitizing effect on the prepared teeth when brought into intimate contact therewith, and (c) a bacteriostatic agent also providing less than 5 percent of the compound and sufficient to prevent noxious odors from forming and to also prevent a proliferation of bacteria from infiltering the restoration and prepared teeth, gingival tissue and other mouth environs during periods of provisional function of the lubricant.

2. A lubricating compound as in claim 1 in which the base is Aqualose and provides at least 90 percent of the compound and a coloring agent which causes the compound to be opaque to the extent that when applied as a thin film the resulting visible color contrast of the compound is seen on gold, silver, porcelain and a prepared tooth.

3. A lubricating compound as in claim 2 in which the coloring agent is zinc oxide of less than 5 percent.

4. A lubricating compound as in claim 1 in which the base includes Solulan 24 or more than 85 percent and Amerchol L 101 of about 10 percent of the compound.

5. A lubricating compound as in claim 1 in which the base is Lipolan of more than 95 percent of the compound and a coloring agent which causes the compound to be opaque to the extent that when applied as a thin film the resulting visible color contrast of the compound is seen on gold, silver, porcelain and a prepared tooth.

6. A lubricating compound as in claim 5 in which the coloring agent is zinc oxide of less than 2 percent.

7. A lubricating compound for the fitting, trial mounting and removal of prosthodontic appliances, said compound including: (a) a stable, non-toxic, non-setting, water soluble, greaseless base material providing at least 80 percent of the compound, said base material being characterized as having a lubricating quality which quality is not materially affected by storage under reasonable conditions and also during intimate contact with the environs of the mouth, appliance and teeth preparations, said base having a consistency sufficiently stiff to prevent fluid flow by gravity; (b) an anti-inflammatory agent provided by hydrocortisone of about 1½ of 1 percent of the compound and sufficient to provide a desensitizing effect on the prepared teeth when brought into intimate conact therewith, and (c) a bacteriostatic agent also providing less than 5 percent of the compound and sufficient to prevent noxious odors from forming and to also prevent a proliferation of bacteria from infiltering the restoration and prepared teeth, gingival tissue and other mouth environs during periods of provisional function of the lubricant.

8. A lubricating compound as in claim 7 in which the base is Aqualose and provides at least 90 percent of the compound and a coloring agent which causes the compound to be opaque to the extent that when applied as a thin film the resulting visible color contrast of the compound is seen on gold, silver, porcelain and a prepared tooth.

9. A lubricating compound as in claim 7 in which the base includes Solulan 24 of more than 85 percent and Amerchol L 101 of about 10 percent of the compound.

10. A lubricating compound as in claim 7 in which the base is Lipolan of more than ninety-five percent of the compound and a coloring agent which causes the compound to be opaque to the extent that when applied as a thin film the resulting visible color contrast of the compound is seen on gold, silver, porcelain and a prepared tooth.

* * * * *

UNITED STATES PATENT OFFICE
CERTIFICATE OF CORRECTION

Patent No. 3,966,925　　　　　　　　Dated June 29, 1976

Inventor(s) Arthur Milton Bell

It is certified that error appears in the above-identified patent and that said Letters Patent are hereby corrected as shown below:

Column 6, line 33, "cottom" should read -- cotton --.

Column 7, line 4, "sulous" should read -- sulcus --.

Claim 4, line 2, "or" should read -- of --.

Claim 7, line 63, "1-1/2 of 1" should read -- one to one and a half --;

line 65, "conact" should read -- contact --.

Signed and Sealed this

Seventh Day of September 1976

[SEAL]

Attest:

RUTH C. MASON　　　　　　　　C. MARSHALL DANN
Attesting Officer　　　　　　　Commissioner of Patents and Trademarks